United States Patent [19]

Liotta et al.

[11] 4,128,399
[45] Dec. 5, 1978

[54] DEVICE AND METHOD FOR DETECTING PHENOTHIAZINE-TYPE DRUGS IN URINE

[76] Inventors: Lance A. Liotta, 6186 Wilson Mills Rd., Mayfield Village, Ohio 44143; Robert S. Weiss, 18316 Newell, Shaker Heights, Ohio 44122

[21] Appl. No.: 667,038

[22] Filed: Mar. 15, 1976

[51] Int. Cl.² .......................................... G01N 31/06
[52] U.S. Cl. .................... 23/230 B; 422/56; 422/69
[58] Field of Search ............... 424/7, 79; 260/2.2 R, 260/2.2 C; 252/408; 23/253 TP

[56] References Cited

U.S. PATENT DOCUMENTS

| | | | |
|---|---|---|---|
| 2,794,786 | 6/1957 | Segal et al. | 424/7 |
| 2,992,166 | 7/1961 | Jizz et al. | 424/7 |
| 3,012,937 | 12/1961 | Schlichting | 424/79 |
| 3,468,636 | 9/1969 | Macleod | 210/25 |
| 3,531,254 | 9/1970 | Okuda | 252/408 |
| 3,915,639 | 10/1975 | Friedberg | 252/408 |

FOREIGN PATENT DOCUMENTS 1255613  12/1971  United Kingdom ................ 424/7

*Primary Examiner*—Joseph L. Schofer
*Assistant Examiner*—Peter F. Kulkosky
*Attorney, Agent, or Firm*—Fay & Sharpe

[57] ABSTRACT

A device and method is provided for the qualitative and semi-quantitative determination of the presence of phenothiazine-type drugs in urine. The article comprises an ion exchange resin which denotes cations in a reaction between a color forming reagent and the phenothiazine-type drug to produce a permanent color change. The intensity of the color change is proportional to the dose concentration.

28 Claims, No Drawings

DEVICE AND METHOD FOR DETECTING PHENOTHIAZINE-TYPE DRUGS IN URINE

BACKGROUND OF THE INVENTION

The present invention relates to an improved device and method for detecting the presence of phenothiazine-type drugs in urine. The device comprises a mass of cation exchange resin having in contact therewith a color reactive reagent which when contacted with a solution containing a phenothiazine-type drug cause a color change to occur.

Phenothiazine and related drugs are presently in wide use throughout medicine and psychiatry in connection with the treatment of certain mental disorders. While there action is still incompletely understood, they are of definite benefit in the treatment of a variety of psychiatric disorders. For example, under systematic chemotherapy, psychotic patients whose illness is characterized by catatonic depressive, or paranoid symptomatology may show remission of symptoms and can be discharged into the community. Unfortunately, the same patients who are most benefited by chemotherapy are most likely to omit intake of their prescribed drug. Consequently, in the treatment of such patients, it is important to provide objective evidence of actual drug intake.

This need to determine drug intake is well known in the art and to accomplish such a purpose a number of methods for detecting the presence of phenothiazine-type drugs in the urine were developed. (See Forrest F. M., Forrest I. S. & Mason A. S., Review of Rapid Urine Tests for Phenothiazine and Related Drugs, American Journal Psychiatry vol. 118: pp. 300–307, 1961). However, all of these methods employed chemical systems which required the use of strong liquid mineral acids, generally at a pH of 1.0 or less, in combination with ferric chloride. The low pH is necessary for the specificity of the test. Because of this requirement for a strong acid solution, these previous methods are generally considered not suitable for safe use by untrained persons on an outpatient basis. Accordingly, there was a need for a safe and efficient device and method for detecting the presence of phenothiazine-type drugs in urine.

This problem of unreliable chemotherapy intake by psychiatric patients was solved in part by the use of injectable slow release compounds such as prolixin tri flu perazine deconate. However, the rate of metabolism and/or effective dosage of these agents varies considerably from one patient to the next. Thus, it is difficult to determine on an individual basis when a new injection is required.

Accordingly, it became apparent that there was a need for a safe urine screening test, preferably in dry "dip stick" form, for the presence of psychophramacologic metabolic products of phenothiazine-type drugs.

Therefore, the primary objective of the presence invention is to provide a device and method for determining the presence of phenothiazine-type drugs in urine which does not require the use of a liquid mineral acid.

Another objective of the present invention is to provide a safe sensitive urine screening test for the metabolic products of injectable slow release phenothiazine-type drugs.

A further objective of this invention is to provide a reagent system for producing a permanent color change in the presence of phenothiazine related drugs. (Previous methods have yielded reactions with transient color changes having a critical reading time).

In addition, another object of the invention is to provide a simple, but accurate and safe, device and method which can be used in the emergency room to determine whether a patient is suffering from an overdose of a phenothiazine related drug.

Other objects of the invention will become apparent to those skilled in the art from a reading of the specification and claims.

The improved device and method of the invention provides a more rapid, accurate, and persisting color change in the presence of these psychopharmacologic agents of the phenothiazine-type than previous methods. Furthermore this method is safe for use by persons not possessing a high level of training and skill in clinical chemistry. More specifically, the method does not require the use of strong liquid acids, as do previously described systems. Accordingly, the present invention overcomes certain problems associated with the prior method and techniques used to determine the presence of phenothiazine-type drugs.

SUMMARY OF THE INVENTION

As used herein and in the appended claims the term "phenothiazine-type drugs" is intended to include the well known group of psychoactive compounds having the general formula:

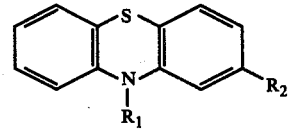

wherein $R_1$ and $R_2$ may be hydrogen or substitute groups therefor. Obviously, the basic phenothiazine molecule may also be modified at other points on the rings.

The most commonly used phenothiazine-type drugs are set forth below together with their structural formula

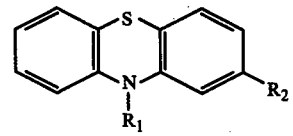

phenothiazine

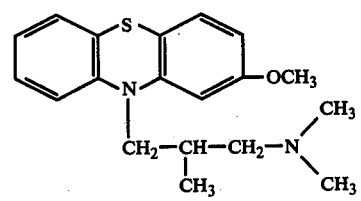

levomepromazine

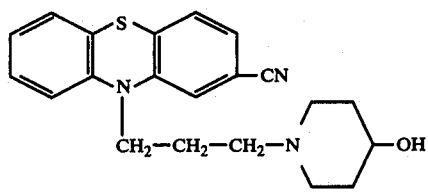

propericiazine

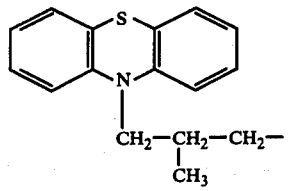

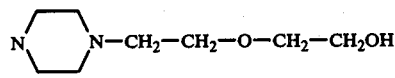

dixyrazine

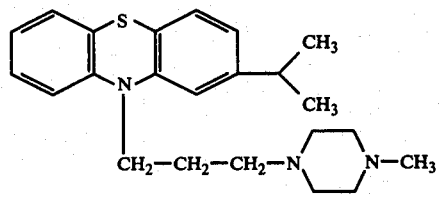

perazine

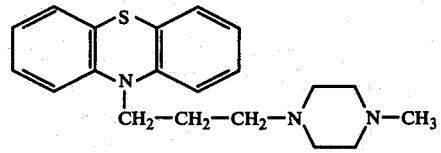

thioproperazine

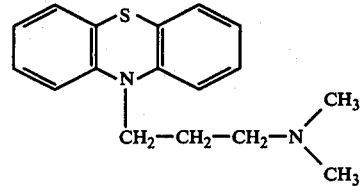

trifluoperazine propthipendyl

One aspect of the invention concerns a device for determining the presence of phenothiazine-type drugs in urine which comprises a supported mass of cation exchange resin having in contact therewith a color forming reagent, with the ion exchange resin and color forming reagent being present in an amount sufficient to cause a color change to occur in the device when it is brought into contact with a urine sample containing a phenothiazine-type drug.

In another aspect it concerns a method for determining the presence of phenothiazine-type drugs in urine comprising contacting a urine specimen with a detecting device comprising a supported mass of cation exchange resin having in contact therewith a color forming reagent, with the ion exchange resin and color forming reagent being present in an amount sufficient to cause a color change to occur in the device when it is brought into contact with a urine sample containing a phenothiazine-type drug.

In a still further aspect the invention concerns a device and method for determining the presence of tricyclic antidepressant compounds of the phenothiazine-type (i.e., derivatives of phenothiazine) in urine by a device which comprises a supported mass of cation exchange resin having in contact therewith a color forming reagent, with the ion exchange resin and color forming reagent being present in an amount sufficient to cause a color change to occur in the device when it is brought into contact with a urine specimen containing a tricyclic anti-depressant compound.

DESCRIPTION OF THE PREFERRED EMBODIMENTS OF THE INVENTION

Broadly stated, the device of the invention, whether it is to be used to determine the presence of phenothiazine-type drugs or tricyclic antidepressants, generally includes a supported mass of cation exchange resin having in contact therewith a suitble color forming regent, with the ion exchange resin and the color forming reagent being present in an amount sufficient to cause a color change to occur in the device when it is brought into contact with a urine specimen containing the drug being tested for.

The preferable cation exchange resin utilized in the practice of the invention is in the form of microspheres. A resin which has been found to be highly satisfactory is Dow AG SOW-X2, hydrogen form. These resins are produced by sulfonating styrene divinylbenzene copolymers with sulfuric acid, and as their method of manufacture is well known in the art it will not be discussed herein. This resin is sized such that the bulk of its particles passed through a 200 mesh screen but are retained on a 400 mesh screen. The ion exchange resin can be positioned on or in suitable support. That is, the ion exchange resin can be placed on a suitable substrate which may be flat or have indentations therein for receiving the resin. The resin can be applied as a lose or compacted material or, if desired, it can be bonded to the support or substrate by a suitable adhesive. All that is required is that the cation exchange resin be free to function in its normal manner, that is, to donate cations. The cation exchange resin can be applied to paper or any other suitable support. In one embodiment of the invention, the ion exchange resin is sandwiched between sheets of porous paper. Obviously, the device of the invention can take many different physical forms. No specific cation resin must be used in the practice of the invention. The main criteria for the cation exchange resin being that it is active enough to product a color change, in conjunction with the color forming reagent, when contacted by a phenothiazine containing urine specimen. This is accomplished by the liberation of an effective amount of cations to obtain a local pH of 1.0 or less.

The color forming reagent can be any substance which causes a color change to occur when used in accordance with the practice of the invention. It can be applied to the ion exchange resin by various well known techniques. A preferred method is to impregnate the resin with an aqueous solution of the reagent. In practice, an aqueous solution of the color forming reagent has been applied to the ion exchange resin and then evaporated to dryness. To date, best results are obtained when the color forming reagent is a heavy metal salt.

When phenothiazine-type drugs are to be detected, the color forming reagent most suitable is one which yields ferric ions. In practice, the material most commonly employed for this purpose is ferric chloride. The exact concentration of ferric ions present is not critical. All that is required is enough ferric ions to produce the desired color change. The most desirable amount of color forming reagent to be utilized in any given situation can be determined emperically.

If a tricyclic antidepressant drug is present, it has been discovered that the most desirable color forming reagents are potassium dichromate, a salt of a rare earth metal, e.g., ceric ammoniumnitrate, and mixtures thereof. Again, in the practice of the invention, various color forming reagents may be utilized provided they produce the desired color change.

While the present invention has been primarily directed to the detection of phenothiazine-type drugs, as noted hereinbefore, it also concerns the detection of tricyclic antidepressants which are closely related thereto. Basically, there are no major structural or chemical differences between the tricyclic anti-depressants and phenothiazine-type antipsychotic agents or drugs. The separate classification comes at the pharmacological and clinical stages of testing. The tricyclic antidepressants are grouped as isosteres of the tricyclic antipsychotics. Isosteres are structures whose important spatial features are similar, although their molecular structures are not identical or even closely related. These two classes differ mainly in the composition of the bridging atoms between the two phenyl groups. (See Clark, W. G., del Guidice, J. *Principles of Psychopharmacology*, Academic Press. Page 172). Phenothiazine-type drugs have a three-ringed structure in which two benzene rings are linked by a suflur and a nitrogen. Generally, the nature of the various substituent groups at positions 2 and 10 influence the pharmacological effect and the generic name of the specific compound. Tricyclic antidepressants of the type concerned differ from the phenothiazine-type drugs only by a replacement of the sulfur with another element or group. For example, imipramine, an anti-depressant of the type concerned is a dibenzozepine derivative of a phenothiazine-type drug in which the sulfur has been replaced by an ethylene linkage. The structural formula of imipramine is as set forth below.

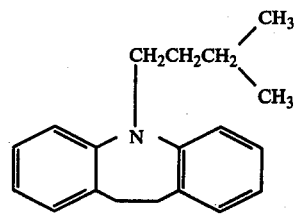

Conventionally, imipramine is tested for in the same manner as a phenothiazine-type drug or compound. That is, a strong acid solution containing potassium dichromate is used with all its attendant problems. The present invention obviates these problems by providing a simple, accurate means for determining its presence in urine.

The present invention can be better understood from the following examples which set forth specific means for practicing the instant invention.

EXAMPLE 1

A plurality of devices for detecting the presence of phenothiazine-type drugs in urine were produced as described below:

About 0.1 gram (about 0.5 ml) of analytical grade cation exchange resin beads were formed into a loose pellet having a thickness of about 1 mm. The cation exchange resin used was Dow AG SOW X2, hydrogen form. The resin was in the form of microspheres and had a particle size distribution in the 200 to 400 mesh range. An aqueous 15% solution of ferric chloride was prepared using distilled water. About 0.2 ml. of this solution (color forming agent) was applied to the surface of the so-formed resin pellet. The solvent for the color forming reagent was then evaporated.

Urine specimens were obtained from patients who were being treated with various phenothiazine-type drugs. These specimens were then tested using the above-described type of device for the presence of such drugs. Table 1 below presents the results of such tests. Column 1 shows the drug dosage given the patient; column 2 shows the color reaction observed; and column 3 shows the color reaction observed when the heretofore standard Forrest test was utilized.

Table 1

| Patient Dosage mg/8 hrs. 1 | Color Reaction by use of device of invention 2 | Color Reaction by conventional Forrest Test 3 |
|---|---|---|
| 1) Thorazine (chloropromazine) | | |
| 250 mg | Dark purple red | Purple |
| 100 mg | Red | Red |
| 25 mg | Light pink | No change |
| 2) Prolixin decanoate (flu phenazine decanoate) | | |
| 50 mg Injected 8 days prior to assay | Pink-red | No change |
| 3) Mellaril (thioridazine) | | |
| 50 mg | Pink-red | Transient pink |

From the above data, it is clear that the subject invention provides a new and improved device and method for determining the presence of phenothiazine-type drugs in urine.

This example shows how the device of the invention can be used to colorimetrically determine the amount of a phenothiazine-type drug present in a given solution.

EXAMPLE 2

A plurality of devices for determining the presence of tricyclic antidepressant compounds (phenothiazine type) were prepared as described in Example 1, except 0.2 ml of an aqueous (distilled water) 20% solution of potassium dichromate was applied to each pellet (the solvent for the color forming reagent can be evaporated, as desired).

Four separate aqueous solutions were prepared with each one containing a different amount of a tricyclic antidepressant drug. This amount of such drug is specified in column 1 of Table 2. These solutions were then tested for the presence of such drugs using the above-described type of device. Table 2 below presents the results of such tests. The drug used was TOFRANIL, generic name imipramine hydrochloride. Column 1 shows the drug dosage, while column 2 shows the color change realized.

Table 2

| Concentration 1 | Color change after 15 minutes 2 |
| --- | --- |
| 1.8 mg/ml | Very dark green (greenish black) |
| 0.18 mg/ml | Dark green |
| 0.018 mg/ml | Green |
| 0.0018 mg/ml | Very light green |

From the above data, it is apparent that the subject invention provides a new and improved device and method for determining the relative amount of tricyclic antidepressant drugs present in the urine of the drug taken.

In addition to the foregoing, the well known drugs Sinequon (dioxepin hydrochloride) and Norpramin (desipramine hydrochloride) were detected in patient's urine by means of a device of the type described in Example 2, except that the color forming reagent was a mixture of equal amounts (10% each) of potassium dichromate and ceric ammoniumnitrate. This mixture of color forming reagents seemed to produce a clearer color than when either reagent was used alone.

The present invention is the result of a series of studies which have shown that a strong cation exchange resin in dense, dry microsphere form can serve as a suitable cation donor for the color reaction between a heavy metal salt (color forming reagent) and a phenothiazine-type drug. No previous publications disclose this technique. The device of the invention is most sensitive when the metallic salt (color forming reagent) and microsphere resin exist at a high local concentration. This affords the lowest local pH (less than about 1) with adequate amounts of color forming reagent at the interface between these two materials.

While the instant invention has been discussed with primary emphasis on the detection of phenothiazine-type drugs, a further objective, as before noted, is to provide a method for the rapid urine screening of tricyclic antidepressants of the dibenzazepine type. These mood elevating agents are widely used in medicine and psychiatry. A major problem in the use of these drugs is that individual patients metabolize the drug differently. The device of the invention facilitates a pharmacological management program directed to the use of these drugs in that it makes the determination of their presence (i.e., use) simpler than prior known techniques.

While there have been described what are at present considered to be the preferred embodiments of this invention, it will be obvious to those skilled in the art that various changes and modifications may be made therein without departing from the invention, and it is, therefore, aimed in the appended claims to cover all such changes and modifications as fall within the true spirit and scope of the invention.

What is claimed is:

1. A device for determining the presence of a phenothiazine-type drug in urine comprising a substrate supporting a mass of cation exchange resin impregnated with a color forming reagent, said ion-exchange resin being present in an amount sufficient to liberate adequate hydrogen ions to cause the solution being tested in the area in immediate contact with said ion-exchange resin to have a pH sufficient to cause said color forming reagent to react with said phenothiazine-type drug, and said color forming reagent being present in an amount sufficient to cause a color change to occur in said device when brought into contact with a urine specimen containing a phenothiazine-type drug.

2. The device of claim 1 wherein said color forming reagent produces ferric ions.

3. The device of claim 3 wherein said color forming reagent is ferric chloride.

4. The device of claim 1 wherein said cation exchange resin is in its hydrogen form.

5. The device of claim 1 wherein said cation exchange resin is present in pellet form.

6. The device of claim 1 wherein said cation exchange resin is present in an amount such that when contacted with a urine specimen the pH of the specimen in immediate contact with said resin is less than about 1.

7. The method of detecting the presence of a phenothiazine-type drug in urine comprising, contacting a mass of cation exchange resin impregnated with a color forming reagent, said ion exchange resin being present in an amount sufficient to liberate adequate hydrogen ions to cause the solution being tested in the area in immediate contact with said ion exchange resin to have a pH sufficient to cause said color forming reagent to react with said phenothiazine-type drug, and said reagent being present in an amount sufficient to cause a color change to occur in said device when brought into contact with a urine specimen containing a phenothiazine-type drug, with urine specimen; and observing any color change therein to determine the presence of a phenothiazine-type drug.

8. The method of claim 7 wherein in said mass of cation exchange resin is positioned on a substrate.

9. The method of claim 7 wherein said color forming reagent produces ferric ions.

10. The method of claim 9 wherein said color forming reagent is ferric chloride.

11. The method of claim 7 wherein said cation exchange resin is in its hydrogen form.

12. The method of claim 7 wherein said cation exchange resin is present in pellet form.

13. The method of claim 7 wherein said cation exchange resin is present in an amount such that when contacted with a urine specimen the pH of the specimen in immediate contact with said resin is less than about 1.

14. A device for determining the presence of tricyclic antidepressant drugs of the phenothiazine-type in urine comprising a substrate supporting a mass of cation exchange resin impregnated with a color forming reagent, said ion-exchange resin being present in an amount sufficient to liberate adequate hydrogen ions to cause the solution being tested in the area in immediate contact with said ion-exchange resin to have a pH sufficient to cause said color forming reagent to react with said phenothiazine-type drug, and said reagent being present in an amount sufficient to cause a color change to occur in said device when brought into contact with a urine specimen containing a tricyclic drug of the phenothiazine-type.

15. The device of claim 14 wherein said color forming reagent is selected from the group consisting of potassium dichromate, ceric ammoniumnitrate and mixtures thereof.

16. The device of claim 15 wherein said color forming reagent is ceric ammoniumnitrate.

17. The device of claim 15 wherein said color forming reagent is potassium dichromate.

18. The device of claim 14 wherein said cation exchange resin is in its hydrogen form.

19. The device of claim 14 wherein said cation exchange resin is present in pellet form.

20. The device of claim 14 wherein said cation exchange resin is present in an amount such that when contacted with a urine specimen the pH of the specimen in immediate contact with said resin is less than about 1.

21. A method of detecting the presence of a tricyclic antidepressant drug of the phenothiazine type in urine which comprises contacting a mass of cation exchange resin impregnated with a color forming reagent, said ion exchange resin being present in an amount sufficient to liberate adequate hydrogen ions to cause the solution being tested in the area in immediate contact with said ion exchange resin to have a pH sufficient to cause said color forming reagent to react with said phenothiazine-type drug, and said regent being present in said device when brought into contact with a urine specimen containing a tricyclic antidepressant drug of the phenothiazine type.

22. The method of claim 21 wherein in said mass of cation exchange resin is positioned on a substrate.

23. The device of claim 21 wherein said color forming reagent is selected from the group consisting of potassium dichromate, ceric ammoniumnitrate and mixtures thereof.

24. The method of claim 21 wherein said color forming reagent is ceric ammoniumnitrate.

25. The method of claim 21 wherein said color forming reagent is potassium dichromate.

26. The method of claim 21 wherein said cation exchange resin is in its hydrogen form.

27. The method of claim 21 wherein said cation exchange resin is present in pellet form.

28. The method of claim 21 wherein said cation exchange resin is present in an amount such that when contacted with a urine specimen the pH of the specimen in immediate contact with said resin is less than about 1.

* * * * *